United States Patent [19]

Sarumar et al.

[11] Patent Number: 4,769,357
[45] Date of Patent: Sep. 6, 1988

[54] PROCESS FOR PRODUCING COMPOSITE OXIDE CATALYST

[75] Inventors: Kohei Sarumar; Yoichi Ishii; Isamu Kobayashi, all of Ami, Japan

[73] Assignee: Mitsubishi Petrochemical Company Limited, Marunouchi, Japan

[21] Appl. No.: 17,582

[22] Filed: Feb. 24, 1987

[30] Foreign Application Priority Data

Feb. 27, 1986 [JP] Japan .................................. 61-42727
Mar. 14, 1986 [JP] Japan .................................. 61-56716

[51] Int. Cl.$^4$ .......................... B01J 21/06; B01J 23/72; B01J 23/84; B01J 23/88
[52] U.S. Cl. .................................... 502/245; 502/244; 502/247; 502/248; 502/249; 502/311; 502/312; 502/335
[58] Field of Search ............... 502/248, 249, 311, 312, 502/244, 245, 247, 335

[56] References Cited

U.S. PATENT DOCUMENTS

| | | | |
|---|---|---|---|
| 4,075,127 | 2/1978 | Kadowaki et al. | 502/312 X |
| 4,290,920 | 9/1981 | Suresh et al. | 502/311 X |
| 4,568,790 | 2/1986 | McCain | 502/312 X |

Primary Examiner—W. J. Shine
Attorney, Agent, or Firm—Oblon, Fisher, Spivak, McClelland & Maier

[57] ABSTRACT

A process for producing a composite oxide catalyst comprising at least Sb, Mo, V and/or Nb by the steps of combining and heating the sources of required respective elements, characterized in that a composite oxide represented by the following formula, which has been heated previously at a temperature of 600° to 900° C., is used as at least a part of a source of Sb supply:

$$Sb_p\text{-}X_q\text{-}Y_r$$

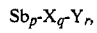

wherein x represents at least one selected from the group consisting of Ni, Fe, Co and Bi; Y represents at least one selected from the group consisting of Al and Si; p is a numeral of 1-40, q is a numeral of 1-20 and r is a numeral of 0-10, provided that when r is 0, Ni of X is at least partly supplied by nickel carbonate.

A catalyst having a large mean pore size is obtained. When the catalyst is used in an oxidation reaction such as air oxidation of acrolein, acrylic acid as the object product can be obtained in high selectivity.

14 Claims, No Drawings

PROCESS FOR PRODUCING COMPOSITE OXIDE CATALYST

BACKGROUND OF THE INVENTION

1. Field of the Art

This invention relates to a process for producing a composite oxide catalyst which comprises at least Sb, Mo, V and/or Nb. More particularly, this invention relates to a process for preparing a composite oxide catalyst characterized primarily by the introducing mode of a specific constituent element, i.e. Sb.

The composite oxide catalyst comprising at least Sb, Mo, V and/or Nb is well known as a catalyst used for vapor phase catalytic oxidation reaction. As the vapor phase catalytic oxidation reaction, there may be specifically mentioned the oxidation reaction of olefins into unsaturated aldehydes or unsaturated carboxylic acids, the oxidation reaction in the presence of ammonia, viz, ammoxydation, of olefins into unsaturated nitriles, the oxidation reaction of unsaturated aldehydes into unsaturated carboxylic acids, the oxidative dehydrogenation reaction of saturated aldehydes or saturated carboxylic acids into unsaturated carboxylic acids, etc.

Obviously from these illustrations, the term "vapor phase catalytic oxidation" should include, in addition to simple oxidation, "ammoxydation" and "oxidative dehydrogenation", which definition should also be accepted in this specification, and it further means that the reaction is conducted in the presence of molecular oxygen such as air and/or oxygen gas.

2. Prior Art

The aforementioned vapor phase catalytic oxidation reaction is often accompanied by undesirable sequential reactions wherein a part of the target product is further oxidized into products with less value added.

It has been long-established that in order to suppress such sequential reactions as far as possible, one of the key points is how to improve the effectiveness factor of a catalyst in the reaction. The improvement of the effectiveness factor of the catalyst coincides with the reduction of the diffusion resistance for reactants in the reaction as far as possible.

It is well known that the shape of catalyst and the pore distribution are the most dominative factors as regards the effectiveness factor of a catalyst. Thus, there have been discussed the relationship between the shape of a catalyst and the effectiveness factor ["KAGAKU KOGAKU" (Chemical Engineering) 30 (2), 73-79 (1966), published by The Soc. Chem. Engineer, Jpn.] and the relationship between the pore distribution and the effectiveness factor ["KAGAKU KOGAKU IV" (Ed. by Shigehumi Fujita & Hei-ichiro Tohata, published in 1963 from TOKYO KAGAKU DOJIN CO.)].

As described above, the composite oxide catalysts each comprising at least Sb, Mo, V and/or Nb is well known in the art and are specifically disclosed in the specifications of Japanese Patent Unexamined Publication Nos. 18823/72, 43922/74 and 23589/77. According to these specifications, nothing may be disclosed about the pore distribution which has to do with the aforementioned effectiveness factor with reference to the preparation of catalyst, but it is described as being advantageous to use Sb and Ni in the form of nickel antimonate. Further, there is disclosed a process for preparing the nickel antimonate by incorporating an Sb source and a nickel source into a composite and subjecting the composite to heat treatment at an elevated temperature. These catalysts can be supported on silica.

SUMMARY OF THE INVENTION

We have found that when nickel carbonate is used as the nickel source in the preparation of the aforementioned nickel antimonate or, in other words, an Sb—Ni—O composite, a composite oxide of Sb—Ni—O having a larger pore size can be obtained whereby a catalyst of an improved selectivity will be produced, and that the similar effect can be observed in the case when Si and/or Al are in advance present in addition to the Sb—Ni—O as well as in the case when merely the latter is used.

Furthermore, we have found that the composite oxide of Sb—Ni—Si—O having a larger pore size can be obtained when silica is added before the heat treatment at an elevated temperature during the preparation of the aforementioned Sb—Ni—O composite whereby an improved catalyst selectivity is obtainable, and that the elements other than Ni which are conducive, when used as an antimonate, to give a catalyst of a high selectivity, include Fe, Co, and Bi.

This invention is based on these findings.

There is thus provided, according to this invention, a process for producing a composite oxide catalyst wherein a composite oxide catalyst comprising at least Sb, Mo, V and/or Nb is produced by a process comprising incorporating sources of required respective elements into a composite and subjecting the composite to heat treatment into the composite oxide catalyst, characterized in that use is made as at least a part of the Sb source of a composite oxide represented by the following formula, which has been heated previously at a temperature of 600° to 900° C.:

$$Sb_p\text{—}X_q\text{—}Y_r,$$

wherein X represents at least one element selected from the group consisting of Ni, Fe, Co and Bi; Y represents at least one element selected from the group consisting of Al and Si; p is a numeral of 1–40, q is a numeral of 1–20 and r is a numeral of 0–10, provided that when r is 0, Ni of X is at least partly supplied by nickel carbonate.

One of the embodiments of this invention is a process for producing a composite oxide catalyst wherein a composite oxide catalyst comprising at least Sb, Mo, V and/or Nb is produced by a process comprising incorporating sources of required respective elements into a composite and subjecting the composite to a heat treatment into the composite oxide catalyst, characterized in that use is made as at least a part of the source of Sb supply of a composite oxide represented by the following formula which has been heated previously at a temperature of 600° to 900° C. and in which at least a part of Ni has been supplied:

$$Sb_p\text{—}Ni_q\text{—}Y_r\text{—}O,$$

wherein Y represents Al and/or Si; p is a numeral of 1–40, q is a numeral of 1–20 and r is a numeral of 0–10.

As another embodiment of this invention, there is provided a process for producing a composite oxide catalyst wherein a composite oxide catalyst comprising at least Sb, Mo, V and/or Nb is produced by a process comprising incorporating the sources of required respective elements into a composite and subjecting the composite to a heat treatment into the composite oxide catalyst, characterized in that use is made as at least a part of the source of Sb supply of a composite oxide represented by the following formula which has been heated previously at a temperature of 600° to 900° C.:

$$Sb_p—X_q—Si_{rr}—O,$$

wherein X represents at least one element selected from the group consisting of Ni, Fe, Co and Bi; p is a numeral of 1–40, q is a numeral of 1–20 and rr is a numeral of 1–10.

This invention is characterized essentially by the use of a specified composite oxide as an Sb source, and a variety of advantages can be obtained thanks to this way of introducing Sb (and other elements) in such a form.

Thus, in the case of the first embodiment above, a composite oxide catalyst of which selectivity has been improved is of a formula of (Sb)—Mo—V and/or Nb—Ni—A—O, wherein A is an element which can be comprised in the catalyst obtained by introducing thereinto Ni in the form of an antimonate, which Ni has once been in the form of a carbonate.

It is well known that Ni is used as a constituent of a composite oxide catalyst. However, it is believed unexpected to have found that when Ni is used as a carbonate, which is then converted into an antimonate to form the Ni source, a composite oxide having a pore size larger than that of a composite oxide by the use of other Ni compound can be obtained thus improving extensively the selectivity of the catalyst obtained (see Comparative Example I series mentioned hereunder). Further it is believed unexpected to have found that a catalyst having high selectivity can also be obtained by preliminarily compounding Si and/or Al into the Sb—Ni—O composite oxide.

The term "antimonate" mentioned above means, in accordance with this invention, a product obtained by a process wherein respective compounds for the source of an element supply have been incorporated into a composite and the composite is subjected to a heat treatment at 600° to 900° C., and accordingly does not necessarily mean an antimonate salt as a chemical compound (it being of no value to confirm the production thereof). Similarly, the "formula" does not mean that the chemical entity represented thereby is a pure chemical compound of the formula.

In the second embodiment mentioned above, on the other hand, a composite oxide catalyst having an improved selectivity of Sb—Mo—V and/or Nb—Z—A—O, wherein Z is an element which can be comprised in the form of an antimonate salt and A is an element which can be comprised in the catalyst, in accordance with the present invention, is obtained by compounding Si into an antimonate salt in accordance with this invention when a certain element as the Z constituent is introduced in the form of an antimonate into the catalyst.

It is well known that silica is used as a support of a composite oxide catalyst. However, it is believed unexpected to have found that when silica is present in the course of the formation of an antimonate salt, a composite oxide having a pore size larger than pore sizes that the original antimonate salt and the silica respectively have inherently possessed can be obtained thus improving extensively the selectivity of the catalyst obtained (see Comparative Example II series mentioned hereunder). Further it is believed unexpected that this technique can be applied also to Fe, Co, Ni and Bi and a catalyst having high selectivity can also be obtained.

The term "formation of the antimonate salt" mentioned above means, in accordance with this invention, a product obtained by a process wherein respective compounds for the source of element supply have been incorporated into a composite and the composite is subjected to a heat treatment at 600° to 900° C., and does not necessarily mean the formation of an antimonate salt as a chemical compound (it being of no value to confirm the production thereof). Similarly, the "formula" does not mean that the chemical entity represented thereby is a pure chemical compound of the formula.

DETAILED DESCRIPTION OF THE PREFERRED EMBODIMENT

EMBODIMENT I

Catalyst and Preparation Thereof

Basic Catalyst

The catalyst according to this invention belongs to the category of composite oxide catalysts comprising at least Sb, Mo, V and/or Nb. The series of this catalyst can be schematically represented by the following formula, which illustrates only components:

$$Sb—Mo—V \text{ and/or } Nb—Ni—A—O,$$

wherein A represents an element which can be comprised in the catalyst, and specifically represents W, Cu, Fe, Co or the like. The catalyst of this type is usually used in the form of an intimate contact with a carrier material such as silica, alumina, a refractory oxide or the like. However, these carrier components and the catalyst components are often undistinguishable from each other, and therefore the Si and Al in the aforementioned silica and alumina can be considered as the components of A.

Such composite oxide catalysts are well known in the art as mentioned above, and thus the composition and the method of production of the catalyst in this invention may be any of those suitable except for the improvement inherent to this invention. The production is preferably carried out basically by a step of incorporating simultaneously or stepwise the sources of catalyst component elements supply into a composite, during which step a carrier material will be introduced when a carried catalyst is to be produced, and finally a step of subjecting the composite to a heat treatment. As a matter of course, the shape of the catalyst is preferably such that the Aris radius will be smaller for obtaining the higher effectiveness factor.

Source of Antimony Supply

The source of antimony supply which is used for introducing Ni (as well as Si and/or Al, if necessary) into the aforementioned basic catalyst according to this invention is a composite oxide represented by the formula Sb—Ni—O or Sb—Ni—Y—O, wherein Y represents Si and/or Al, which composite oxide has previously been heated at a temperature of 600° to 900° C. and is obtained by using nickel carbonate at least partly as the source of Ni supply to the composite oxide. The composite oxide, which is a composite oxide in nature, can be prepared by the aforementioned process with respect to the basic catalyst. Specifically, as for the starting materials, there may be used a metallic antimony, antimony oxide and the like as the source of Sb supply; nickel carbonate as a source of Ni supply; colloidal silica, granular silica and the like as the source of Si supply and alumina and the like as the source of Al supply, and as for the process there may be conducted that powder of antimony pentoxide or trioxide and silica or alumina are added to an aqueous slurry of nickel carbonate and the mass is evaporated to dryness with stirring and the solid product is calcined in the presence of air at a temperature of 600° to 900° C., preferably 650° to 850° C. It should be understood that "nickel carbonate" as an essential element of this invention includes basic nickel carbonate.

If the calcined solid is not produced in powder, it is ground to an appropriate extent and used at least as the part of the source of Sb supply for the catalyst of this invention.

The atomic ratios of this composite oxide, i.e. w-z in $Sb_w$—$Ni_x$—$Y_y$—$O_z$, wherein Y represents Si and/or Al, are preferably as follows:

w: 1-40, preferably 1-20,
x: 1-20, preferably 1-10,
y: 0-10, preferably 0-5 and
z: a numeral determined by the degree of oxidation of respective components.

Preparation of the Catalyst in Embodiment I

The catalyst according to this invention can be produced by the process for producing the composite oxide catalyst mentioned above except that at least a part of the source of Sb supply is the aforementioned composite oxide Sb—Ni—(Y)—O. It is preferred to supply the aforementioned composite oxide to an extent of at least 25%, preferably 50%-100%, of the Sb of the finished catalyst.

Referring to an embodiment of the preparation of the catalyst, composite oxide powder Sb—Ni—(Y)—O obtained as above is wet-mixed with a poly acid of Mo, V or Nb (e.g., molybdatic acid or phosphomolybdic acid) or salt thereof (e.g., ammonium salt), a hydroxide or salt of these metals, and an optional component (e.g., the aforementioned component A), such as a copper compound, a tungsten compound, a phosphorus compound, an alkaline earth compound or the like, and the mixture is concentrated, dried and pulverized. The powder thus obtained is formed together with a suitable support or an excipient such as silica, graphite, Avicel or the like into a shape of particles, cylinders, tablets, rings, etc. by the methods of tableting extrusion or the like and then heated at a temperature of ca. 300° to 500° C. for a period of 1-10 hours to give a composite oxide catalyst. In this case, heating is preferably is carried out in the non-reductive atmosphere, particularly in the presence of molecular oxygen.

The catalyst of this invention thus obtained has a composition represented schematically by the following formula:

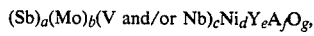

$(Sb)_a(Mo)_b(V \text{ and/or } Nb)_c Ni_d Y_e A_f O_g,$ wherein Y represents Si and/or Al, A represents an optional component element such as Cu, W, Fe, Co, or mixtures thereof and a-g represent the following values:
a: 1-100, preferably 10-100,
b: 1-100, preferably 1-50,
c: 0.1-50, preferably 1-20,
d: 1-100, preferably 10-100,
e: 0-200, preferably 0-100,
f: 0.1-50, preferably 1-20 and
g: a numeral determined by the degree of oxidation of respective component elements.

The catalyst according to this invention thus obtained has mostly a pore size of 5,000 Å or more. By contrast, conventional catalyst obtained by a method other than that according to this invention has a mean pore size of 400 to 1,000 Å. The term "mean pore size" means a value measured with a porosimeter by the mercury method, thus indicating the pore size at the maximum value on the differential curve.

USE OF CATALYST

The catalyst according to this invention is used in a vapor phase catalytic oxidation reaction to give object compound in high selectivity. The vapor phase catalytic oxidation reaction, as mentioned above, has a meaning over a wide range including ammoxydation and oxidative dehydrogenation.

In one of the preferred application of the catalyst according to this invention, it is used for the oxidation of acrolein or methacrolein to give acrylic acid or methacrylic acid. In other words, the typical use of the catalyst of this invention is for the second step in the two step preparation of an unsaturated carboxylic acid such as acrylic acid or methacrylic acid by the oxidation of a corresponding olefin, that is propylene or isobutene, wherein the first step is for oxidation of the olefin into unsaturated aldehyde, that is acrolein or methacrolein, and the second step is for oxidation of the unsaturated aldehyde into the unsaturated carboxylic acid. In passing, as the catalyst used for the vapor phase catalytic oxidation reaction in the first step, there is mentioned a well known composite oxide catalyst comprising Mo and Bi, which is extensively used industrially. Further, it is also well known that such a composite oxide catalyst comprising Mo and Bi is very useful for ammoxydation and oxidative dehydrogenation reaction.

EMBODIMENT II

Basic Catalyst

The catalyst according to Embodiment II of this invention belongs to the category of composite oxide catalysts comprising at least Sb, Mo, V and/or Nb. The type of this catalyst can be schematically represented by the following formula:

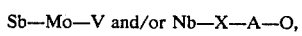

Sb—Mo—V and/or Nb—X—A—O, wherein X represents an element which has been introduced in the form of an antimonate salt, specifically, Fe, Co, Ni or Bi; A represents an optional element, and specifically represents W, Cu or the like. The catalyst of this type is usually used in the form of an intimate contact with a carrier material such as silica, alumina, a refractory oxide or the like. However, these components and the catalyst components are often undistinguishable to each other, and therefore the Si in the aforementioned silica can be considered as the components of A.

Such composite oxide catalyst are well known in the art as mentioned above, and thus the composition and the method of production of the catalyst in this invention may be any of those suitable except the improvement inherent to this invention. The production is preferably carried out basically by a step of incorporating simultaneously or stepwise the sources of catalyst component element supplies into a composite, during which step a carrier material will be introduced when a carried catalyst is to be produced, and finally a step of subjecting the composite to a heat treatment. As a matter of course, the shape of the catalyst is preferably such that the Aris radius will be smaller for making the higher effectiveness index.

Source of Antimony Supply

The source of antimony supply which is used for introducing Fe, Co, Ni and Bi into the aforementioned basic catalyst according to this invention is a composite oxide represented by the formulae Sb—X—Si—O, wherein X represents at least one of the elements selected from the group consisting of Fe, Co, Ni and Bi, which composite oxide has previously been heated at a temperature of 600° to 900° C.

The composite oxide, which is a composite oxide in nature, can be prepared by the aforementioned process with respect to the basic catalyst. Specifically, as for the starting materials, there may be used a metallic antimony, antimony oxide and the like as the source of Sb supply; nitrates, chlorides or the like of Fe, Co, Ni and Bi as a source of supply thereof; and colloidal silica, granular silica and the like as the source of Si supply, and as for the process, there may be conducted that powder of antimony trioxide and silica are added to an aqueous solution of iron nitrate (or a nitrate salt of Co, Ni or Bi) and the mass is evaporated to dryness with stirring and the solid product is calcined in the presence of air at a temperature of 600° to 900° C., preferably 650° to 850° C. It should be understood that "nickel carbonate" as an essential element of this invention includes a basic nickel carbonate.

If the calcined solid is not produced in powder, it is ground to an appropriate extent and used at least as the part of the source of Sb supply for the catalyst of this invention.

The atomic ratios of this composite oxide, i.e. w-z in $Sb_w$—$X_x$—$Si_y$—$O_z$, wherein X represents Fe, Co, Ni and/or Bi, are preferably as follows:

w: 1–40, preferably 1–20,
x: 1–20, preferably 1–10,
y: 1–10, preferably 1–5 and
z: a numeral determined by the degree of oxidation of respective components.

Preparation of the Catalyst in Embodiment II

The catalyst according to this invention can be produced by the process for producing the composite oxide catalyst mentioned above except that at least a part of the source of Sb supply is the aforementioned composite oxide Sb—X—Si—O. It is preferred to supply the aforementioned composite oxide to an extent of at least 25%, preferably 50% to 100%, of the Sb of the finished catalyst.

Referring to an embodiment of the preparation of the catalyst, powder of composite oxide Sb—X—Si—O obtained as above is wet-mixed with a poly acid of Mo, V or Nb (e.g., molybdic acid or phosphomolybdic acid) or salt thereof (e.g., ammonium salt), a hydroxide or salt of these metals and an optional component (e.g. the aforementioned component A), such as a copper compound, a tungsten compound, a phosphorus compound, an alkaline earth compound or the like, and the mixture is concentrated, dried and pulverized. The powder thus obtained is formed together with a suitable support or an excipient such as silica, graphite, Avicel or the like in the shape of particles, cylinders, tablets, rings, etc. by the methods of tableting, extrusion or the like and then heated at a temperature of ca. 300° to 500° C. for a period of 1–10 hours to give a composite oxide catalyst. In this case, heating is preferably is carried out in the non-reductive atmosphere, particularly in the presence of molecular oxygen.

The catalyst of this invention thus obtained has a composition represented schematically by the following formula:

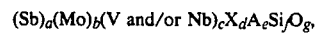

$(Sb)_a(Mo)_b(V \text{ and/or } Nb)_cX_dA_eSi_fO_g,$ wherein X represents Fe, Co, Ni or Bi, A represents an optional component element such as Cu, W or mixture thereof, and a–g represent the following values:

a: 1–100, preferably 10–100,
b: 1–100, preferably 1–50,
c: 0.1–50, preferably 1–20,
d: 1–100, preferably 10–100,
e: 0.1–50, preferably 1–20,
f: 1–100, preferably 1–100 and
g: a numeral determined by the degree of oxidation of respective component elements.

The catalyst according to this invention thus obtained has a mean pore size of 2,000 Å or more. By contrast, conventional catalyst obtained by a method other than that according to this invention has a mean pore size of 400 to 1,000 Å. The term "mean pore size" means a value measured with a porosimeter by the mercury method, thus indicating the pore size at the maximum value on the differential curve.

Use of Catalyst

The catalyst according to this Embodiment II is used in a vapor phase catalytic oxidation reaction to give object compound in high selectivity. The vapor phase catalytic oxidation reaction, as mentioned above, has a meaning over a wide range including ammoxydation and oxidative dehydrogenation.

With respect to the use of the catalyst in the Embodiment II, there can be applied the aforementioned description for the catalyst in the Embodiment I entirely.

EXPERIMENTAL EXAMPLES

Example I-1

In 300 ml of pure water was dispersed 228 g of basic nickel carbonate ($NiCO_3.2Ni(OH)_2.4H_2O$). To this mixture, 50 g of silica ("CARPLEX #67") and 150 g of antimony trioxide were added and thoroughly agitated. The slurry was heated, concentrated and dried. Then the solid obtained was calcined in a muffle furnace at 800° C. for 3 hours. The calcined product, Sb—Ni—Si—O, was ground so that particles pass through a sieve of 60 mesh.

Pure water (540 ml) was heated to ca. 80° C., and 8.1 g of antimony paratungstate, 63.9 g of ammonium paramolybdate, 8.4 g of ammonium metavanadate and 2.8 g of cuprous chloride were sequentially added and dissolved. Then, the powder of the aforementioned Sb—Ni—Si—O was added to this solution and thoroughly agitated and mixed.

The slurry was heated to a temperature of 80° to 100° C., concentrated and dried. The dried product was ground so that particles pass through sieve of 24 mesh, and 1.5% by weight of graphite was added and mixed.

Then, the mixture was loaded on a small size tableting machine to form tablets of a size of 5×4 hmm.

The tablets were calcined in a muffle furnace at 400° C. for 5 hours to make a catalyst.

The catalyst thus obtained had a composition represented by the following atomic ratios:

Sb:Ni:Si:Mo:V:W:Cu = 100:43:80:35:7:3:3.

The catalyst (50 ml) was charged in a stainless-steel reaction tube equipped with a jacket for a nitrate heating media and the catalytic oxidation reaction of acrolein was carried out. The raw material gas comprised 4% of acrolein, 46% of steam and 50% of air and was passed through the reaction tube at a space velocity of 870 h$^{-1}$ at a 0° C. basis. At a nitrate temperature of 250° C., the conversion of acrolein was 99.3%, the yield of acrylic acid was 97.6% and the selectivity to acrylic acid was 98.3%.

Example I-2

In 400 ml of pure water was dispersed 228 g of basic nickel carbonate. To this mixture, 159 g of antimony trioxide and 11.1 g of α-alumina were added with agitation. The slurry was heated, concentrated and dried. Then the solid obtained was calcined in a muffle furnace at 800° C. for 2 hours.

The calcined product, Sb—Ni—Al—O, was ground so that particles pass through a sieve of 60 mesh.

Pure water (540 ml) was heated to ca. 80° C., and 63.9 g of ammonium paramolybdate, 8.4 g of ammonium metavanadate, 4.6 g of niobium hydroxide and 21.2 g of copper sulfate were sequentially added and dissolved. Then, the powder of the aforementioned Sb—Ni—Al—O was added slowly to this solution and thoroughly agitated and mixed. The catalyst was prepared in the same manner as in Example I-1.

The catalyst thus obtained had a composition represented by the following atomic ratios:

Sb:Ni:Al:Mo:V:Nb:Cu = 100:43:20:35:7:3:9.

When the same reaction as in Example I-1 was carried out with the use of the catalyst, the conversion of acrolein was 99.7%, the yield of acrylic acid was 97.0% and the selectivity to acrylic acid was 97.3% at a reaction temperature of 250° C.

Example I-3

To 300 ml of pure water was dispersed 228 g of basic nickel carbonate. To this mixture, 159 g of antimony trioxide was added with agitation. Then the slurry was heated, concentrated and dried. Then the solid obtained was calcined in a muffle furnace at 800° C. for 3 hours.

The calcined product, Sb—Ni—O, was ground so that particles pass through a sieve of 60 mesh.

The catalyst having the following composition was prepared by operating in the same manner as in Example I-2:

Sb:Ni:Mo:V:Nb:Cu = 100:43:35:7:3:9.

When the reaction was carried out in the same manner as in Example I-1 by the use of the catalyst, the conversion of acrolein was 99.4%, the yield of acrylic acid was 97.4% and the selectivity to acrylic acid was 98.0% at a reaction temperature of 250° C.

COMPARATIVE EXAMPLE I-1

A catalyst having the same composition as that in Example I-1 was prepared in the same manner as in Example I-1 except that 136 g of nickel nitrate dissolved in 90 ml of warm water was used in place of nickel carbonate as a raw material of Ni in the preparation of Sb—Ni—Si—O in Example I-1, and the reactivity was evaluated under the same condition as above.

The conversion of acrolein was 98.4%, the yield of acrylic acid was 94.7% and the selectivity to acrylic acid was 96.2% at a reaction temperature of 250° C.

COMPARATIVE EXAMPLE I-2

A catalyst having the same composition as that in Example I-3 was prepared in the same manner as in Example I-3 except that 136 g of nickel nitrate dissolved in 90 ml of warm water was used in place of nickel carbonate as a raw material of Ni in the preparation of Sb—Ni—O in Example I-3, and the reactivity was evaluated under the same condition as above.

The conversion of acrolein was 98.1%, the yield of acrylic acid was 93.0% and the selectivity to acrylic acid was 94.8% at a reaction temperature of 250° C.

EXAMPLE II-1

In 90 ml of warm water was dissolved 136 g of nickel nitrate. To this mixture, 50 g of silica ("CARPLEX #67") and 159 g of antimony trioxide were added slowly with stirring. The slurry was heated, concentrated and dried at 90° C. Then the solid obtained was calcined in a muffle furnace at 800° C. for 3 hours. The calcined product, Sb—Ni—Si—O, was ground so that particles pass through a sieve of 60 mesh.

Pure water (540 ml) was heated to ca. 80° C., and 8.1 g of ammonium paratungstate, 63.9 g of ammonium paramolybdate, 8.4 g of ammonium metavanadate and 7.8 g of cuprous chloride were sequentially added and dissolved. Then, the powder of the aforementioned Sb—Ni—Si—O was added to this solution and thoroughly agitated and mixed.

The slurry was heated to a temperature of 80° to 100° C., concentrated and dried. The dried product was ground so that particles pass through sieve of 24 mesh, and 1.5% by weight of graphite was added and mixed. Then, the mixture was loaded on a small size tableting machine to form tablets in a size of 5×4 hmm.

The molded product was calcined in a muffle furnace at 400° C. for 5 hours to make a catalyst.

The catalyst thus obtained had a composition represented by the following atomic ratios:

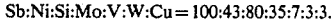
Sb:Ni:Si:Mo:V:W:Cu = 100:43:80:35:7:3:3.

The catalyst (50 ml) was charged in a stainless-steel reaction tube equipped with a jacket for a nitrate heating medium and the catalytic oxidation reaction of acrolein was carried out. The raw material gas comprised 4% of acrolein, 46% of steam and 50% of air and was passed through the reaction tube at a space velocity of 870 h$^{-1}$ at a 0° C. basis. At a nitrate bath temperature of 250° C., the conversion of acrolein was 98.3%, the yield of acrylic acid was 94.7% and the selectivity to acrylic acid was 96.2%.

COMPARATIVE EXAMPLE II-1

In 90 ml of warm water was dissolved 136 g of nickel nitrate. To this mixture, 159 g of antimony trioxide was added slowly with stirring. The slurry was heated, concentrated and dried at 90° C. Then the solid obtained was calcined in a muffle furnace at 800° C. for 3 hours. The calcined product, Sb—Ni—Si—O, was ground so that particles pass through a sieve of 60 mesh.

Pure water (540 ml) was heated to ca. 80° C., and 8.1 g of ammonium paratungstate, 63.9 g of ammonium paramolybdate, 8.4 g of ammonium metavanadate and 2.8 g of cuprous chloride were sequentially added and dissolved. Then, the powder of the aforementioned Sb—Ni—O was added to this solution and thoroughly agitated and mixed. Then 50 g of silica ("CARPLEX #67") was added and mixed thoroughly by stirring. A catalyst was prepared in the same manner as in Example II-1, and the reactivity was evaluated under the same condition.

At a nitrate bath temperature of 270° C., the conversion of acrolein was 97.9%, the yield of acrylic acid was 91.2% and the selectivity to acrylic acid was 93.2%.

EXAMPLE II-2

With the use of 189 g of ferric nitrate in place of 136 g of nickel nitrate in Example II-1, a catalyst was prepared and the reactivity was evaluated below in the same manner as above.

The composition of the catalyst thus obtained is as follows:

Sb:Fe:Si:Mo:V:W:Cu=100:43:80:35:7:3:3.

At a nitrate bath temperature of 260° C., the conversion of acrolein was 99.9%, the yield of acrylic acid was 94.2% and the selectivity to acrylic acid was 94.3%.

EXAMPLE II-3

With the use of 136 g of cobalt nitrate in place of 136 g of nickel nitrate in Example II-1, Sb—Co—Si—O powder was prepared in the same manner.

Then, 540 ml of pure water was heated to ca. 80° C., and 63.9 g of ammonium paramolybdate, 8.4 g of ammonium metavanadate, 4.6 g of niobium hydroxide [NbO(OH)$_3$] and 5.6 g of cuprous chloride were sequentially added with stirring, dissolved and mixed. To this solution, the aforementioned Sb—Co—Si—O powder was gradually added and mixed thoroughly with stirring. The catalyst having the following composition was obtained in the same manner as in Example II-1:

Sb:Co:Si:Mo:V:Nb:Cu=100:43:80:35:7:3:6.

With the use of this catalyst, the catalytic oxidation reaction of acrolein was carried out in the same manner as in Example II-1.

At a nitrate bath temperature of 260° C., the conversion of acrolein was 99.9%, the yield of acrylic acid was 95.2% and the selectivity to acrylic acid was 95.3%.

EXAMPLE II-4

To 700 ml of conc. nitric acid, 133 g of metallic antimony was added portionwise and oxidized. After the evolution of nitric acid gas had stopped, 277 g of bismuth nitrate was added and stirred thoroughly. Then, 125 g of silica sol (containing 20% of SiO$_2$: SNOWTEX N) was added, and the mixture was concentrated with heating and dried. The product was calcined in air at 800° C. for 3 hours and then ground (Sb—Bi—Si—O powder). Pure water (540 ml) was heated to ca. 80 C, and 63.9 g of ammonium paramolybdate, 8.4 g of ammonium metavanadate, 4.6 g of niobium hydroxide and 21.2 g of copper sulfate were sequentially dissolved and mixed with stirring. Then, the powder of the aforementioned Sb—Bi—Si—O was added slowly to this solution and thoroughly mixed. The catalyst having the following composition was obtained in the same manner as in Example II-1:

Sb:Bi:Si:Mo:V:Nb:Cu=100:43:40:35:7:3:9.

With the use of this catalyst, the catalyst oxidation reaction of acrolein was carried out in the same manner as in Example II-1.

At a nitrate bath temperature of 260° C., the conversion of acrolein was 99.2%, the yield of acrylic acid was 92.6% and the selectivity to acrylic acid was 93.3%.

EXAMPLE II-5

With the use of 68 g of nickel nitrate and 68 g of cobalt nitrate in place of 136 g of nickel nitrate in Example II-1, Sb—Ni—Co—Si—O powder was prepared in the same manner. The preparation of catalyst and the evaluation of reactivity were carried out in the same manner.

The catalyst thus obtained had the following composition:

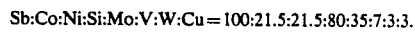

Sb:Co:Ni:Si:Mo:V:W:Cu=100:21.5:21.5:80:35:7:3:3.

At a nitrate bath temperature of 260° C., the conversion of acrolein was 99.9%, the yield of acrylic acid was 94.9% and the selectivity to acrylic acid was 95.0%.

What is claimed is:

1. A process for preparing a mixed metal oxide catalyst comprising at least the elements of Mo, Sb, V and/or Nb which comprises:
   (a) preparing an antimony based composite oxide of the formula: Sb$_p$Ni$_q$Y$_r$O, wherein Y is Al, Si or mixtures thereof; p is a number ranging from 1 to 40, q is a number ranging from 1 to 20 and r is 0–10, by combining raw materials of elements which constitute the composite oxide which include a nickel raw material of which at least a portion is nickel carbonate and then heating the combined materials to a temperature ranging from 600° to 900° C.; and
   (b) combining the raw materials which contain at least the elements Mo, Sb, V and/or Nb of said mixed oxide catalyst, with at least a portion of the raw material which provides antimony for the catalyst being the antimony based composite oxide of step (a), and heating the mixed raw materials to prepare the mixed oxide catalyst.

2. The process according to claim 1, wherein the composite oxide represented by the formula Sb$_p$—Ni$_q$—Y$_r$—O is prepared by evaporating to dryness an aqueous slurry comprising antimony oxide and nickel carbonate and, if necessary, silica and/or alumina and calcining the solid product obtained at 600° to 900° C. in the presence of air.

3. The process according to claim 2, wherein the calcining temperature is between 650° to 850° C.

4. The process according to claim 1, wherein the composite oxide represented by the formula Sb$_p$—Ni$_q$—Y$_y$—O is represented by the following composition:

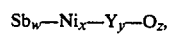

Sb$_w$—Ni$_x$—Y$_y$—O$_z$, wherein w, x, y and z have the meanings as follows:

w: 1-20,
x: 1-10,
y: 0-5 and
z: a number determined by the degree of oxidation of the respective ingredients.

5. The process according to claim 1, wherein the mean pore size of the composite oxide catalyst is at least substantially 5,000 Å.

6. The process according to claim 1, wherein the composite oxide catalyst is represented by the composition:

$$Sb_a\text{—}Mo_b\text{—}(V \text{ and/or } Nb)_c\text{—}Ni_d\text{—}Y_e\text{—}A_f\text{—}O_g,$$

wherein Y represents Si, Al, or mixtures thereof; A represents an element selected from the group consisting of W, Cu, Fe, Co, or mixtures thereof; and a-g have the following values:
a: 1-100,
b: 1-100,
c: 0.1-50,
d: 1-100,
e: 0-200,
f: 0.1-50 and
g: a number determined by the degree of oxidation of the respective ingredients.

7. The process according to claim 6, wherein a-f represent the following values:
a: 10-100,
b: 1-50,
c: 1-20,
d: 10-100,
e: 0-100 and
f: 1-20.

8. A process for preparing a mixed metal oxide catalyst comprising at least the elements of Mo, Sb, V and/or Nb, which comprises:
(a) preparing an antimony based composite oxide of the formula: $Sb_pX_qSi_{rr}O$, wherein X is at least one element selected from the group consisting of Ni, Fe, Co and Bi; p is a number ranging from 1 to 40, q is a number ranging from 1 to 20 and rr is a number ranging from 1 to 10, by combining raw materials of elements which constitute the composite oxide and then heating the combined materials to a temperature ranging from 600° to 900° C.; and
(b) combining the raw materials which contain at least the elements Mo, Sb, V and/or Nb of said mixed oxide catalyst, with at least a portion of the raw material which provides antimony for the catalyst being the antimony based composite oxide of step (a), and heating the mixed raw materials to prepare the mixed oxide catalyst.

9. The process according to claim 8, wherein the composite oxide represented by the formula $Sb_p$—$X_q$—$Si_{rr}$—O is prepared by evaporating to dryness an aqueous slurry consisting of antimony trioxide, a nitrate or chloride of an element selected from the group consisting of Fe, Co and Ni, and silica and calcining the solid product obtained at 600° to 900° C. in the presence of air.

10. The process according to claim 9, wherein the calcining temperature is in the range of 650° to 850° C.

11. The process according to claim 10, wherein the composite oxide represented by the formula $Sb_p$—$X_q$—$Si_{rr}$—O is represented by the following composition:

$$Sb_w\text{—}Ni_x\text{—}Si_y\text{—}O_z,$$

wherein w, x, y and z have the meanings as follows:
w: 1-20,
x: 1-10,
y: 1-5 and
z: a number determined by the degree of oxidation of the respective ingredients.

12. The process according to claim 8, wherein the mean pore size of the composite oxide catalyst is at least substantially 2,000 Å.

13. The process according to claim 8, wherein the mixed oxide catalyst has the formula:

$$Sb_a\text{—}Mo_b\text{—}(V \text{ and/or } Nb)_c\text{—}X_d\text{—}A_e\text{—}Si_f\text{—}O_g,$$

wherein A is an element selected from the group consisting of Cu, W, or mixture thereof, and a-g have the following values:
a: 1-100,
b: 1-100,
c: 1-50,
d: 1-100,
e: 0.1-50,
f: 1-100 and
g: a number determined by the degree of oxidation of the respective ingredients.

14. The process according to claim 13, wherein a-f have the following meanings:
a: 10-100,
b: 1-50,
c: 1-20,
d: 10-100,
e: 1-20 and
f: 10-100.

* * * * *

UNITED STATES PATENT AND TRADEMARK OFFICE
CERTIFICATE OF CORRECTION

PATENT NO. : 4,769,357

DATED : Sep. 6, 1988

INVENTOR(S) : Kohei SARUMARU et al.

It is certified that error appears in the above-identified patent and that said Letters Patent is hereby corrected as shown below:

On the Title Page, Item [75]:

The first inventor's name is misspelled; should read as follows:

-- Kohei Sarumaru --

Signed and Sealed this

Seventh Day of February, 1989

Attest:

DONALD J. QUIGG

*Attesting Officer*      *Commissioner of Patents and Trademarks*